US00PP17263P2

(12) United States Plant Patent
Danziger

(10) Patent No.: US PP17,263 P2
(45) Date of Patent: Dec. 5, 2006

(54) **MINI *IMPATIENS* PLANT NAMED 'IMMICHERO'**

(50) Latin Name: *Impatiens walleriana*
Varietal Denomination: Immichero

(75) Inventor: Gabriel Danziger, Beit Dagan (IL)

(73) Assignee: Syngenta Seeds B.V., Enkhuizen (NL)

( * ) Notice: Subject to any disclaimer, the term of this patent is extended or adjusted under 35 U.S.C. 154(b) by 15 days.

(21) Appl. No.: 11/221,483

(22) Filed: Sep. 8, 2005

(51) Int. Cl.
*A01H 5/00* (2006.01)

(52) U.S. Cl. ..... Plt./317
(58) Field of Classification Search ..... Plt./317
See application file for complete search history.

*Primary Examiner*—Kent Bell
*Assistant Examiner*—Annette H Para
(74) *Attorney, Agent, or Firm*—Bruce Vrana

(57) ABSTRACT

A new and distinct cultivar of mini *Impatiens* plant characterized by its small carmine red flowers, freely flowering habit, dark green foliage, and bushy shaped growth habit with excellent basal branching.

1 Drawing Sheet

Latin name of the genus and species of the plant claimed: *Impatiens walleriana.*
Varietal denomination: 'Immichero'.

BACKGROUND OF THE NEW PLANT

The present invention comprises a new and distinct mini *Impatiens* plant botanically known as *Impatiens walleriana* and referred to by the cultivar name 'Immichero.'

The new cultivar was developed in a controlled breeding program in Beit Dagan, Israel. The new mini *Impatiens* cultivar is characterized by small carmine red flowers, freely flowering habit, dark green foliage, and bush shaped growth habit with excellent basal branching.

The new cultivar is propagated from cuttings resulting from the cross in March 1998 of the proprietary mini *Impatiens* selection identified as 'FRA 200' as female parent and the proprietary mini *Impatiens* selection identified as 'BGA 201' as male parent. 'FRA 200' is not commercially available and has not been patented. 'BGA 201' is not commercially available and has not been patented.

As a result of this cross the present cultivar was selected in February 1999 in Beit Dagan, Israel and has been repeatedly asexually reproduced by cuttings over a period of several years. The distinctive characteristics of this new mini *Impatiens* are stable and reproduced true to type in successive generations of asexual reproduction. It takes 6 to 8 weeks to produce a finished plant, starting from a rooted plug and planted in a 10 cm pot, depending on the temperature.

SUMMARY OF THE INVENTION

The following traits have been repeatedly observed and are determined to be the unique characteristics of 'Immichero.' These characteristics in combination distinguish 'Immichero' as a new and distinct mini *Impatiens* cultivar:

1. Small, carmine red flowers
2. Bushy shaped growth habit with many flowers on top of the foliage
3. Dark green foliage
4. Excellent basal branching Plants of the new mini *Impatiens* differ primarily from the plants of the female parent selection in the following characteristics:

Plants of the new mini *Impatiens* have small carmine red flowers, whereas the plants of the female have small lilac flowers.

Plants of the new mini *Impatiens* differ primarily from the plants of the male parent selection in the following characteristics:

Plants of the mini *Impatiens* have small carmine red flowers, whereas the plants of the male have larger, mid purple flowers.

Plants of the new mini *Impatiens* can be compared to plants of 'Danchesal,' disclosed in U.S. Plant Pat. No. 14,741. In side-by-side comparisons in Enkhuizen, Netherlands, the plants of the new mini *Impatiens* differed from plants of the cultivar 'Danchesal' in the following characteristics:

1. Plants of the new mini *Impatiens* have dark green leaves, whereas plants of the cultivar 'Danchesal' have green leaves
2. Plants of the new mini *Impatiens* have carmine red flowers of about 2.5 cm, whereas the cultivar 'Danchesal' has salmon rose flowers of about 3 cm.

DESCRIPTION OF THE DRAWING

This new mini *Impatiens* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new mini *Impatiens.* The data which defines these characteristics were collected from asexual reproductions carried out in Enkhuizen, Netherlands. The plant history was taken on 20 week old plants, blossomed under natural light in the field.

Color readings were taken in the laboratory under ambient light. Color references are primarily to The R.H.S. Colour Chart of The Royal Horticultural Society of London.

The plant:
*Classification.*—Botanical: *Impatiens walleriana.*
Parentage:
*Female parent.*—Proprietary *Impatiens walleriana* selection identified as code number 'FRA 200,' not patented.
*Male parent.*—Proprietary *Impatiens walleriana* selection identified as code number 'BGA 201,' not patented.
Propagation:
*Type cutting.*—Terminal cuttings.
*Time to initiate roots.*—About 10–21 days at 22–23 degrees C.
*Time to produce a rooted cutting.*—About 28 days at 16–24 degrees C.
*Root description.*—Fine, fibrous, and white in color.
Plant description:
*General appearance.*—Compact, upright, outwardly spreading and mounded plant habit.
*Growth and branching habit.*—Vigorous and freely branching growth habit lateral branches potentially forming at every node, dense and bushy shaped growth habit. Pinching enhances branching.
*Plant height.*—About 18 cm.
*Plant diameter or spread.*—About 37 cm.
Lateral branch description:
*Length.*—About 12 cm.
*Diameter.*—About 8 mm.
*Internode length.*—About 7–25 mm.
*Texture.*—Smooth, glabrous.
*Color.*—From the bottom RHS 58A Red-purple til top 146B Yellow-green.
Foliage description:
*Arrangement.*—Alternate, simple.
*Length.*—About 2.5 cm.
*Width.*—About 1.8 cm.
*Shape.*—Ovate.
*Apex.*—Acuminate.
*Base.*—Attenuate.
*Margin.*—Slightly crenate with minute ciliation.
*Texture, upper and lower surfaces.*—Smooth, glabrous.
*Venation pattern.*—Pinnate.
*Color.*—Developing and fully expanded foliage, Upper surface: RHS 137B Green. Developing and fully expanded foliage, Lower surface: RHS 138B Green with anthocyanic spots RHS 60B.
*Venation, upper and lower surfaces.*—RHS 148A Yellow-green.
Petiole:
*Length.*—About 1.3 cm.
*Diameter.*—About 2 mm.
*Texture, upper and lower surfaces.*—Smooth, glabrous.
*Color.*—RHS 148C Yellow-green.
Flower description:
*Flower type and habit.*—Numerous small single flowers.
*Flowers arise from leaf axils.*—Freely flowering, usually about 25 flowers and flower buds per lateral branch.
*Flower position.*—Above the foliage and typically face upright or outward.
*Flowers lasting.*—About 5–7 days on the plant under greenhouse conditions.
*Flowers.*—Persistent and not fragrant.
*Flowering season.*—Continuous through the spring and summer.
*Height.*—About 2.5 cm.
*Diameter.*—About 2.5 cm.
*Depth.*—About 7 mm.
Flower buds:
*Length.*—About 7 mm.
*Diameter.*—About 4 mm.
*Shape.*—Ovoid.
*Color.*—RHS 138B Green with 61B Red-purple.
Petals:
*Quantity/arrangement.*—Five per flower in a single whorl.
*Length, banner petal.*—About 1 cm.
*Length, lateral petals.*—About 1.1 cm.
*Length, basal petals.*—About 1.5 cm.
*Width, banner petal.*—About 1 cm.
*Width, lateral petals.*—About 8 mm.
*Width, basal petals.*—About 8 mm.
*Shape.*—Obovate to ovate.
*Apex.*—Rounded or slightly emarginate.
*Base.*—Attenuate.
*Margin.*—Entire.
*Texture, upper and lower surfaces.*—Smooth, glabrous.
*Petal color.*—Upper surface: When opening: RHS 53C Red. Lower surface: When opening: RHS 53D Red. Fully opened, banner petal, upper surface: RHS 53C Red. Fully opened, lateral petals, upper surface: RHS 53C Red. Fully opened, basal petals, upper surface: RHS 53C Red. Fully opened, lower surface: RHS 53D Red.
Sepals:
*Quantity/arrangement.*—Five in a single whorl, one modified into an elongated spur.
*Sepal length.*—About 3 mm.
*Sepal diameter.*—About 1 mm.
*Shape.*—Ovate.
*Apex.*—Acute.
*Margin.*—Entire.
*Texture, upper and lower surfaces.*—Smooth, glabrous.
*Color, upper and lower surfaces.*—RHS 148C Yellow-green.
*Spur length.*—About 2.5 cm.
*Spur diameter.*—At flower, about 5 mm, at apex, less than 1 mm.
*Spur color.*—RHS 54C Red at flower, at apex RHS 53C Red.
Peduncles:
*Length.*—About 1.5 cm.
*Diameter.*—About 1 mm.
*Angle.*—About 45° from vertical.
*Strength.*—Strong.
*Texture.*—Smooth, glabrous.
*Color.*—RHS 148C Yellow-green.
Reproductive organs:
*Stamens.*—
*Quantity.*—Five fused around stigma.
*Anther length.*—About 2 mm.
*Anther color.*—RHS 64B Red-purple.
*Pollen amount.*—None observed.
*Pistils — Quantity per flower.*—One.
*Pistil length.*—About 3 mm.
*Stigma shape.*—Rounded.

*Stigma color.*—RHS 64B Red-purple.

*Style color.*—RHS 139A Green.

*Ovary color.*—RHS 139A Green.

*Seed/fruit.*—Seed and fruit production has not been observed.

Disease and pest resistance: Plants of the new *Impatiens* have not been observed to be resistant to pathogens and pests common to *Impatiens.*

What is claimed is:

1. A new and distinct cultivar of mini *Impatiens* plant named 'Immichero', as substantially illustrated and described herein.

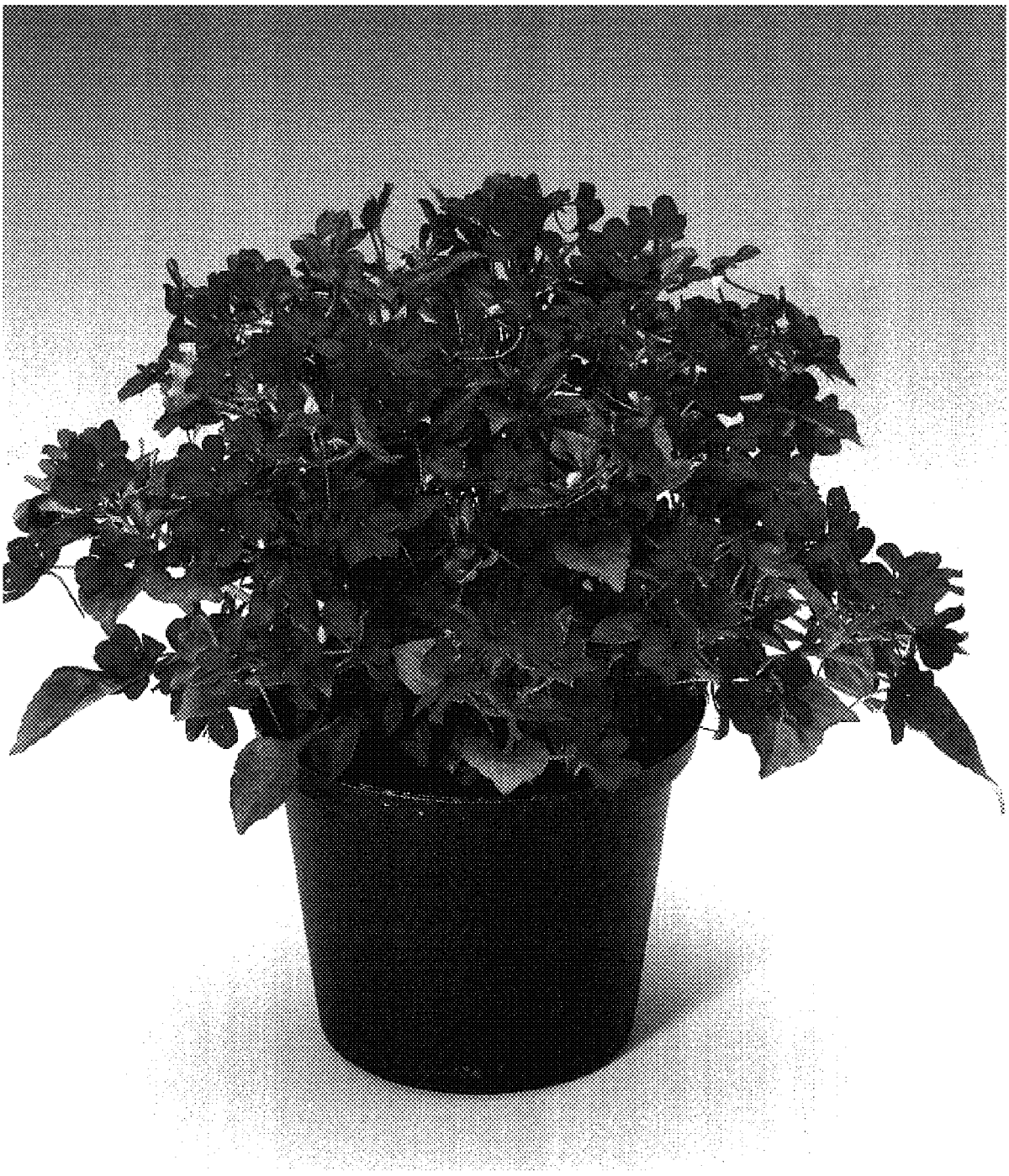

* * * * *